United States Patent
Schwarz

(10) Patent No.: US 9,354,205 B2
(45) Date of Patent: May 31, 2016

(54) METHOD AND SENSOR MOUNT FOR MEASURING SEAM PEAKING IN PIPES BY MEANS OF ULTRASONIC INSPECTION

(75) Inventor: Axel Schwarz, Weingarten (DE)

(73) Assignee: NDT GLOBAL GMBH & CO. KG, Stutensee (DE)

( * ) Notice: Subject to any disclaimer, the term of this patent is extended or adjusted under 35 U.S.C. 154(b) by 291 days.

(21) Appl. No.: 14/237,501

(22) PCT Filed: Jul. 13, 2012

(86) PCT No.: PCT/EP2012/002950
§ 371 (c)(1),
(2), (4) Date: Feb. 6, 2014

(87) PCT Pub. No.: WO2013/020628
PCT Pub. Date: Feb. 14, 2013

(65) Prior Publication Data
US 2014/0230554 A1 Aug. 21, 2014

(30) Foreign Application Priority Data
Aug. 6, 2011 (DE) .................. 10 2011 109 717

(51) Int. Cl.
*G01N 29/04* (2006.01)
*G01N 29/07* (2006.01)
(Continued)

(52) U.S. Cl.
CPC ............... *G01N 29/07* (2013.01); *G01B 17/02* (2013.01); *G01N 29/225* (2013.01); *G01N 29/265* (2013.01); *G01N 2291/2636* (2013.01)

(58) Field of Classification Search
CPC ... G01N 29/07; G01N 29/225; G01N 29/265; G01N 29/043; G01N 29/262; G01N 2291/2636
USPC ............................................ 73/592, 622–629
See application file for complete search history.

(56) References Cited

U.S. PATENT DOCUMENTS 4,006,359 A * 2/1977 Sullins .................. G01M 3/005
104/138.2
4,285,243 A 8/1981 Collingwood
(Continued)

FOREIGN PATENT DOCUMENTS

DE 30 34 319 C2 9/1980
DE 301 770 B5 11/1993
(Continued)

OTHER PUBLICATIONS

International Preliminary Report on Patentability issued Feb. 11, 2014 in related application PCT/EP2012/002950, 8pages.
(Continued)

*Primary Examiner* — Helen Kwok
(74) *Attorney, Agent, or Firm* — Carter, DeLuca, Farrell & Schmidt, LLP; Robert P. Michal

(57) ABSTRACT

For ultrasonic measurement of pipe seam peaking, optionally with simultaneous ultrasonic wall thickness measurement using ultrasonic probes mounted on sensor holders on a sensor mount, it is proposed to use a sensor mount with sensor holders mounted on movable skids, which are pressed outward by spring elements and bear against the internal pipe surface, and skids having a large skid breadth greater than the seam peak breadth measured in the pipe's circumferential direction in the region of a measured seam peak, and sensor holders equipped with sensors only in a measuring region situated half way between two skid contact surfaces, wherein the measuring region breadth is less or equal to half of the skid breadth such that the stand off deviation of the sensors resulting in the seam peak region remains below a threshold value.

23 Claims, 9 Drawing Sheets

Figure 1:
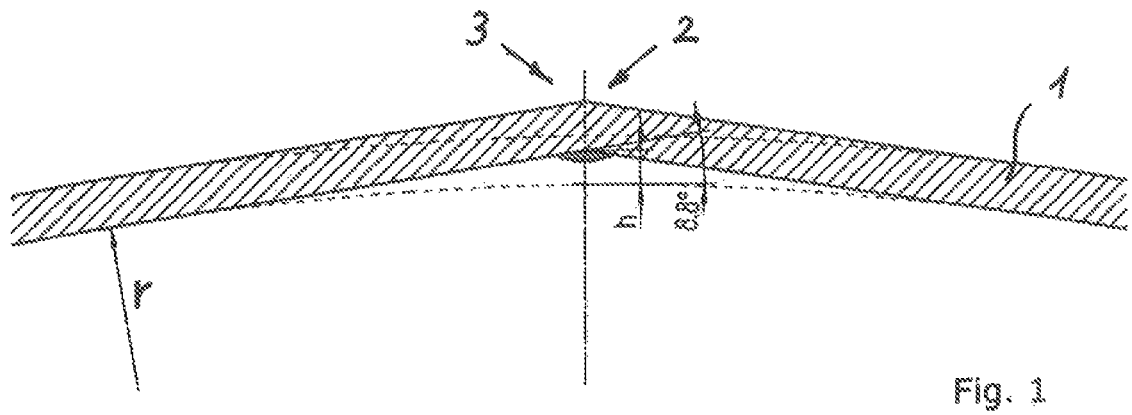

(51) Int. Cl.
  *G01B 17/02* (2006.01)
  *G01N 29/22* (2006.01)
  *G01N 29/265* (2006.01)

(56) References Cited

U.S. PATENT DOCUMENTS

| | | | |
|---|---|---|---|
| 4,964,059 A | 10/1990 | Sugaya | |
| 5,097,710 A * | 3/1992 | Palynchuk | G01N 29/28 |
| | | | 73/644 |
| 5,583,292 A * | 12/1996 | Karbach | G01N 29/223 |
| | | | 73/588 |
| 6,848,313 B2 | 2/2005 | Krieg | |
| 7,168,322 B2 * | 1/2007 | Bardoux | B23K 31/12 |
| | | | 73/588 |
| 7,236,255 B2 * | 6/2007 | Kodama | B21C 37/0811 |
| | | | 219/121.63 |
| 7,900,517 B2 * | 3/2011 | Chougrani | G01N 29/043 |
| | | | 73/592 |
| 8,079,265 B2 * | 12/2011 | Brignac | G01N 29/226 |
| | | | 73/618 |
| 8,104,347 B2 * | 1/2012 | Den Boer | G01N 29/07 |
| | | | 73/596 |
| 2001/0017541 A1 | 8/2001 | Kwun | |
| 2003/0136195 A1 | 7/2003 | Krieg | |

FOREIGN PATENT DOCUMENTS

| | | |
|---|---|---|
| DE | 38 53 323 T2 | 3/1995 |
| DE | 102 62 232 B4 | 7/2008 |

OTHER PUBLICATIONS

English language translation of International Preliminary Report on Patentability issued Feb. 11, 2014 in related application PCT/EP2012/002950, 10 pages.

Sanierung einer Rohölpipeline, Verfahren und Bewertungskriterien Hans-Jörg Schmidt und Wolfgang Schmidt; 5. Symposium Pipelinetechnik—2002 Köln; 3R International, vol. 41, No. 2, 2002, p. 106-112, ISSN 0340-3386.

Bruchmechanische Bewertung von längsnahtgeschweißten Rohren mit hoher Aufdachung; Gerhard Pusch; Carl Hanser München; MP Materialprüfung 47 (2005) 1-2, p. 70-76.

Foulds J.R. et al: "Concerns about seam-welded piping at elevated temperatures", 1996, Proceedings of SPIE—The International Society for Optical Engineering—Nondestructive Evaluation of Utilities and Pipelines 1996 SPIE US, vol. 2947, pp. 67-77, XP002685322.

International search report of the European Patent Office dated Nov. 2, 2012 with enclosures, including written opinion (12 pages).

\* cited by examiner

METHOD AND SENSOR MOUNT FOR MEASURING SEAM PEAKING IN PIPES BY MEANS OF ULTRASONIC INSPECTION

CROSS REFERENCE TO RELATED APPLICATIONS

This application is a U.S. National Phase Application under 35 USC 371 of International Application PCT/EP2012/002950 filed Jul. 13, 2012, which claims priority from German Application No. DE 10 2011 109 717.5 filed Aug. 6, 2011, the entire disclosure of each of which is incorporated herein by reference.

The invention relates to a method for measuring seam peaking in a pipe, more particularly in a pipeline, by means of ultrasonic measurement with the aid of ultrasonic probes, which are mounted on sensor holders on a sensor mount, which mount is moved in a direction of transport through the pipe. The invention further relates to an appropriate sensor mount.

DD 301 770 B5 discloses an inline inspection tool for ascertaining damaged areas of pipe walls according to the eddy current method. This method entails the use of a ring mount with staggered rows of eddy current sensors, which are individually pressed against the internal wall of the pipe by means of spring-biased yokes. The measurement system described in said publication can recognize cracks and corrosion sites but is unable to measure seam peaking in the pipe. The sensors are positioned such that they plunge into the seam peaks to ensure that they bear against the pipe wall being tested. Thus it is impossible to measure the degree of seam peaking, that is, the deviation from geometric circularity of the pipe wall.

DE 30 34 319 C2 describes an inspection device for ascertaining cracks in pipes. The ultrasonic sensors used for this purpose are pressed against the internal surface of the pipe by means of springs. The measurement system described in this publication can recognize cracks by ultrasonic means but is unable to measure seam peaking in the pipe. The number of ultrasonic sensors employed is too small and thus the resolution is too low to allow measurement of seam peaking to be carried out. In addition, measurement of seam peaking is impossible since the ratio of sensor holder width to testing area width is almost 1.

DE 38 53 323 T2 discloses devices for ultrasonic examination of an oil pipe, which allow for detection and localization of deformed regions of, and wall thickness faults in, a pipe. The measurement system described in this publication measures the distance from the pipe wall by means of ultrasonic sensors and can thus measure the contour of the pipe. A rigid sensor ring is used to scan the pipe wall. The disadvantages of these devices are a stand off that is too large, poor resolution due to the large stand off, and measurement inaccuracies occurring when the device is not centrally positioned. The system is suitable for detecting dents but is too inexact for the measurement of seam peaking.

DE 102 62 232 B4 describes a method and device for testing pipes for corrosion, pitting, and cracks. To this end, measuring sensors are disposed on an inline inspection tool such that complete signal coverage of the circumference of the pipe is achieved. The measuring system described in this publication can recognize cracks and regions of corrosion by ultrasonic means, but it is unable to measure seam peaking in the pipe, since the construction of the sensor mount has complete coverage as its goal. The skids are thus only broad enough to be able to accommodate all sensors necessary for complete coverage. The skids would plunge into a seam peak and would be unable to measure its true depth.

During the fabrication of longitudinally welded pipes, manufacturing related deviations from circularity, termed seam peaking, arise in the region of the welded seam. These deviations from theoretical circularity become even greater when the pipe is subjected to pressure stresses, e.g. during a pressure test, and the development of cracks in and around the welded seam can become enlarged, leading to leakage of the pipe or pipeline. It is known that seam peaking has a predominant influence on the fatigue performance of pipes. This is in principle a consequence of increased tension due to the notching effect created by seam peaking. In addition, cracks within a seam peak have more serious effects, leading to premature failure of the pipe. The coincidence of a high seam peak and a crack is to be regarded as being a critical situation. As such, cracks of only 0.1 mm depth, which would have sufficient security reserve, when they lie outside a seam peak, become critical when they appear in the region of a high seam peak of approximately 6 mm.

The measurement of cracks in a welded seam showing a high seam peak is only possible to a limited extent due to the geometrical situation, since the intromission angle can vary to a large extent. For example, in the case of a seam peak of 6 mm in a 40 inch diameter pipeline it can vary, theoretically, by up to 8.8°. Consequently, the security of pipelines is often determined by means of a stress test involving an increase in pressure. These static or cyclic tests are not non-destructive, since pipes that are damaged will burst. But even pipes that do not burst are further damaged by the stress test and their remaining useful life is shortened.

In order to minimize the elaboration and expense of these stress tests, attempts are being made to measure seam peaking using an intelligent inline inspection tool. Comparative values reveal maximum acceptable seam peaking. Measurement of seam peaking is currently achieved with inline inspection tools having ultrasonic sensors mounted on a rigid ring and adapted to measure wall thickness. The extent of seam peaking is calculated from the measured stand off. The measurement of seam peaking with inline inspection tools having ultrasonic sensors adapted to measure wall thickness is known in the prior art. Instead thereof the usual method of measuring wall thickness involves inline inspection tools having sensor mounts that have sensor holders which are mounted on movable, flexible skids that are spring biased radially outward in order to bear against the internal surface of the pipe, for the measurement of seam peaking the ultrasonic sensors are disposed on a rigid, cylindrical sensor mount. The maximum seam peaking in each individual pipe in a pipeline can be measured in terms of the time taken between the emission of the ultrasonic wave from the sensor and its echo when entering the pipe wall, termed the stand off time, the rigid sensor mount serving as the reference profile for the stand off time. The seam peaking can, for example, be determined individually for each pipe by ascertaining the difference between the maximum seam peaking occurring directly adjacent to the longitudinal welded seam and the averaged seam peaking measured in a region at, say, 30° to the right or to the left of the welded seam.

The paper "Sanierung einer Rohölpipeline—Verfahren and Bewertungskriterien" ["*Restoration of a crude oil pipeline—methods and assessment criteria*"], H.-J. Schmidt and W. Schmidt, 5th Symposium Pipelinetechnik, 2002, Cologne, reveals such a prior art seam peaking method of measurement involving an inline inspection tool having ultrasonic sensors adapted to measure wall thickness, which inline inspection tool has said ultrasonic sensors mounted on a fixed ring. It roughly corresponds to the publication DE 38 53 323 T2 mentioned above.

This prior art method for measuring seam peaking suffers from the drawback that the weight of the inline inspection tool causes a slight degree of eccentricity ranging from approximately 2 to 4 mm, or correspondingly, causes the sensor mount to move away from the center line of the pipe, making precise evaluation more difficult. Due to the weight of the inline inspection tool, the measurement cannot be taken from the center of the pipe, and the values determined for the stand off need to be corrected by the use of comparative values. The overall measurement of the seam peaking thus becomes inexact, and since the severity of a given crack increases with the height of a seam peak, more pipeline's pipes would need to be replaced, for security reasons, than would have been necessary when using an exact method of measuring seam peaking. Thus, with inexact seam peaking measurements, the threshold value for seam peaking or pipe replacement, as needs to be adhered to for security reasons, will have to be adjusted in such a manner that more pipes than necessary will be replaced.

A further drawback of this prior art method of measuring seam peaking using ultrasonic sensors disposed on a rigid ring, relates to the field of application or utilization of this method. The rigid sensor mount makes it more difficult for the inline inspection tool to pass through the pipeline. Pipelines often have pipes showing different wall thicknesses and accordingly having differing inside diameters. T-connectors or outlets having a smaller inside diameter than the straight pipes are also installed. Furthermore, the pipes may have dents, in such cases, an inline inspection tool having a rigid sensor mount either cannot be used due to the inability to pass by the constriction or the diameter of the ring must be reduced, causing an increase in the stand off and a consequent increase in inaccuracy. If a constriction, such as a dent, has to be cut out and replaced by a new pipe, to enable the inline inspection tool to pass by, this will entail high costs for the pipeline operator. Thus, a drawback of a rigid sensor mount is its absence of size reducibility. This is the capacity of the inline inspection tool, or of the sensor mount, to pass through constrictions or diameter reductions in the pipe. It is specified as a percentage of the outside diameter and, for practical applications, should advantageously be in the region of approx. 85%.

Furthermore, as the prior art inline inspection tool passes through the pipeline, the long stand off and the thus prolonged ultrasonic transit time mean that it must proceed at a low speed. This likewise entails increased downtime costs for the pipeline operator during measurement. A further drawback is that the prior art rigid sensor mount allows only geometrical measurement, namely the measurement of seam peaking. A simultaneous measurement of the wall thickness cannot be carried out and a separate run of the inline inspection tool is necessary for this purpose. This also leads to increased downtime costs for the pipeline operator resulting from this measurement.

A further problem is the inaccuracy that arises for geometrical reasons. To determine seam peaking in a pipe using an ultrasonic measuring method, the so-called stand off, that is, the distance from the ultrasonic sensor to the internal surface of the pipe, is measured and from this value the distance to an exactly circular pipe is subtracted. To ensure that the measurement method be as accurate as possible, the stand off should be independent of the position of the ultrasonic sensors and of the position of the skids carrying the ultrasonic sensors. This is, however, only true for a circular pipe not exhibiting seam peaking. Depending on the position of the skid relative to a seam peak, a pipe with seam peaking may allow the skids to plunge into a peak. As a result, the sensors on the skids move slightly radially outward towards the internal pipe wall, and the measured stand off will be smaller than the "real stand off" that would result. If the skids were not to plunge into the peak, thus deviating from a circular arrangement. The error thus produced is the stand off deviation. This denotes the deviation of the stand off from a theoretically exact value that would have occurred in the case of circular geometry and without interference by seam peaking. The stand off deviation depends on the width of the seam peak and the position of the skid. Since the position of the skid relative to the seam peak is indefinite, the theoretical maximum stand off deviation, calculated on a geometrical basis, needs to be taken into account as a seam peaking measurement error, a fundamental inaccuracy, when evaluating the measurement.

In the case of a fundamentally inexact measurement of seam peaking, according to the prior art, the stand off deviation is, as a rule, insignificant, since the theoretical maximum stand off deviation that needs to be taken into account is smaller than the other inaccuracies. In the case of precise seam peaking measurement, however, the maximum stand off deviation should be minimized, in order not to contribute too much inaccuracy to the measurement and to allow a truly exact statement to be made regarding the extent of seam peaking.

Based on this prior art, it is an object of the present invention to provide a method and an appropriate sensor mount for seam peaking measurement in a pipe, more particularly in a pipeline, which yields more accurate results and a wider field of application or utilization on account of the size reducibility of the sensor mount used, and which allows concurrent measurement of the wall thickness. The stand off deviation is desirably to be reduced or minimized.

According to the invention, this object is achieved by a method for ultrasonic measurement comprising the features defined in the attached claim 1. Preferred embodiments, improvements and uses of the invention are revealed in the co-ordinated and dependent claims and in the following description with respective drawings.

A method according to the invention for measuring seam peaking in a pipe, more particularly in a pipeline, by means of ultrasonic measurement with the aid of ultrasonic probes mounted on sensor holders attached to a sensor mount, which is moved in a direction of transport through the pipe, is characterized in that a sensor mount is used, on which sensor holders are mounted on movable skids, which skids are pressed radially outward by means of spring elements so as to cause them to bear against the internal surface of the pipe, such that the sensor mount has a size reducibility and such that the sensors are at a fixed stand off from the internal surface of the pipe except for the region of a seam peak, skids are used that have a large skid breadth, which is greater than the seam peak breadth measured in the circumferential direction of the pipe in the region of a seam peak to be measured, and the sensor holders are equipped in each case with sensors only in a measuring region that is situated half way between two skid contact surfaces, wherein the breadth of the measuring region is smaller than, or equal to, half of the skid breadth, such that the stand off deviation of the sensors resulting in the region of a seam peak remains below a specified threshold value, and the sensor mount comprises at least three successive rings, which rings are disposed one behind the other as regarded in the direction of transport of the sensor mount and have sensors carried by sensor holders, wherein the sensors are disposed on the respective rings with a track distance and the sensors on the succeeding rings are in a gap-covering manner in staggered relationship to each other, thus achieving full coverage of the tracks over the circumference of the pipe.

A sensor mount according to the invention for carrying out a method of the invention for measuring seam peaking in a pipe, which sensor mount is movable through the pipe in a direction of transport and which sensor mount has sensor holders, these having ultrasonic probes attached to them for carrying out an ultrasonic measurement, is characterized in that the sensor mount has movable skids, to which the sensor holders are attached and has spring elements, by means of which the skids are pressed radially outward so as to cause them to bear against the internal surface of the pipe, such that the sensor mount demonstrates size reducibility and such that the sensors are at a fixed stand off from the internal surface of the pipe when outside a region of a seam peak, wherein the skids have a large skid breadth that is greater than the seam peak breadth measured in the circumferential direction of the pipe in the region of a seam peak to be measured, and the sensor holders are equipped in each case with sensors only in a measuring region that is situated halfway between two skid contact surfaces, wherein the breadth of the measuring region is smaller than, or equal to, half of the skid breadth, such that the stand off deviation of the sensors resulting in the region of a seam peak remains below a specified threshold value, and the sensor mount comprises at least three successive rings, which rings are disposed one behind the other as regarded in the direction of transport of the sensor mount and have sensors carried by sensor holders, wherein the sensors are disposed on the respective rings with a track distance and the sensors on the succeeding rings are in a gap-covering manner in staggered relationship to each other, thus achieving full coverage of the tracks over the circumference of the pipe.

An inline inspection tool according to the invention for carrying out measurement of seam peaking in a pipe, more particularly in a pipeline, is characterized in that it includes at least one sensor mount according to the invention.

The advantages of the invention reside in the fact that the measurement is more exact, that a size reducibility of the sensor mount used allows for a wider field of application or utilization for this measuring method, and that concurrent measurement of wall thickness is possible.

The invention allows, for example, for measurement of seam peaking in a pipe having a diameter from 25 cm to 135 cm. Standard pipeline diameters can usually be, say, 34 inches or 40 inches. According to the invention, the sensor mount with its skids, and more particularly the sensor holders, can be configured such that with any desired orientation (rotated or turned) of the sensor holder towards the seam peak, the theoretical stand off deviation is very small, for example, less than 0.25 mm, or preferably less than 0.18 mm. Further, the stand off can be made sufficiently small for it to be included in the range for an optimal wall thickness measurement, so that the wall thickness measurement can be carried out concurrently with the seam peaking measurement. Consequently the invention allows to choose a stand off which enables a simultaneous measurement of the wall thickness of the pipe, so that the seam peaking measurement can be carried out concurrently with the wall thickness measurement. Typical seam peaks of practical significance that can be measured according to the invention are for example smaller than 6 mm and preferably smaller than 5 mm. The breadth of the measuring region can, in preferred embodiments, be between 5% and 50% of the breadth of the skid, in more preferred embodiments between 10% and 45% of this breadth, and in particularly preferred embodiments, between 20% and 35% of this breadth.

The size reducibility of a sensor mount for seam peaking measurement configured according to the invention can be equal to that of a usual sensor mount for wall thickness measurement, for example 85%.

The sensors for seam peaking measurement, according to the invention, are not attached to a fixed, rigid sensor holder ring, but are rather on skids, which skids are interconnected by springs and can follow the pipe wall at a constant distance therefrom. As such, in the context of the size reducibility of the sensor mount, the stand off is independent of the diameter of the pipe. The skids have a stand off optimized for wall thickness measurement, so that the two measurements can be carried out simultaneously. The precisely defined short stand off and the small stand off deviation thus make it possible to simultaneously measure seam peaking and wall thickness.

As is usual for sensor mounts used for wall thickness measurement, the skids are suspended on springs and can follow the course of the pipe wall. This ensures consistency of the stand off. Using the extra-wide skids with only a half complement of sensors on the sensor holders allows for measurement of stand off deviation caused by a seam peak at a theoretical accuracy of less than 0.18 mm (in a 6 mm seam peak).

The seam peaking measurement and a wall thickness measurement can thus be carried out simultaneously and the measurement results are directly comparable, that is to say, that for evaluation of the measurement results, there is no longer any need for the results obtained from two runs of the measuring inline inspection tool through a pipeline to be mapped to each other in terms of the angle of turn and the distance run. This simplifies evaluation.

Since the sensor mount has at least three, and preferably four, rings having sensors attached to sensor holders, which rings are disposed one behind the other as regarded in the direction of transport, and which sensors are preferably divided into two groups, of which each constitutes one part of a two-part sensor mount, that is to say, the distribution of the sensors over multiple rings, or correspondingly, over a sensor mount having multiple parts, the same specifications with regard to the ease of passage of the sensor mount through the pipe can be adhered to as is usual for wall thickness measurement. Due to the unrestricted ease of passage, the preparation for this inline inspection tool's run can be carried out in the same way as for a run of a conventional inline inspection tool. A special, separate investigation of the internal diameter of the pipe need not take place. Since no reduction in inline inspection tool speed is necessary for an exact measurement of seam peaking, the costs in terms of downtime and effort for the operator are reduced, in the case of long pipelines (covering more than 100 km), enormous downtime costs arising when measuring or examining the pipeline are thus saved. Due to the fact that the seam peaking measurement and wall thickness measurement are carried out simultaneously, the costs to the operator for preparation of the inline inspection tools run and for downtime are halved.

Since the skids are pressed against the pipe wall by means of springs, ensuring consistency of the stand off, the inline inspection tool can move at a high speed during measurement of seam peaking as is usual during the measurement of wall thickness.

The more accurate guidance of the sensors and the small stand off deviation are conducive to more precise seam peaking measurement, and a security margin to the threshold for replacement of pipes having seam peaking is not necessary.

Thus, in the case of long pipelines, many individual pipes which would otherwise have required replacement, had an inexact measurement of seam peaking been carried out, can continue to be used, thus reducing costs. The more accurately the seam peaking can be measured, the more accurately is it possible to determine the condition of the pipeline.

The invention is explained in greater detail below with reference to the preferred embodiments illustrated in the figures. The characterizing features described therein may be implemented individually or in combination, in order to provide preferred embodiments of the invention identical or identically functioning elements are designated by the same reference signs in the figures and are usually described only once, even though they might be usefully employed in other preferred embodiments.

Figure 2:
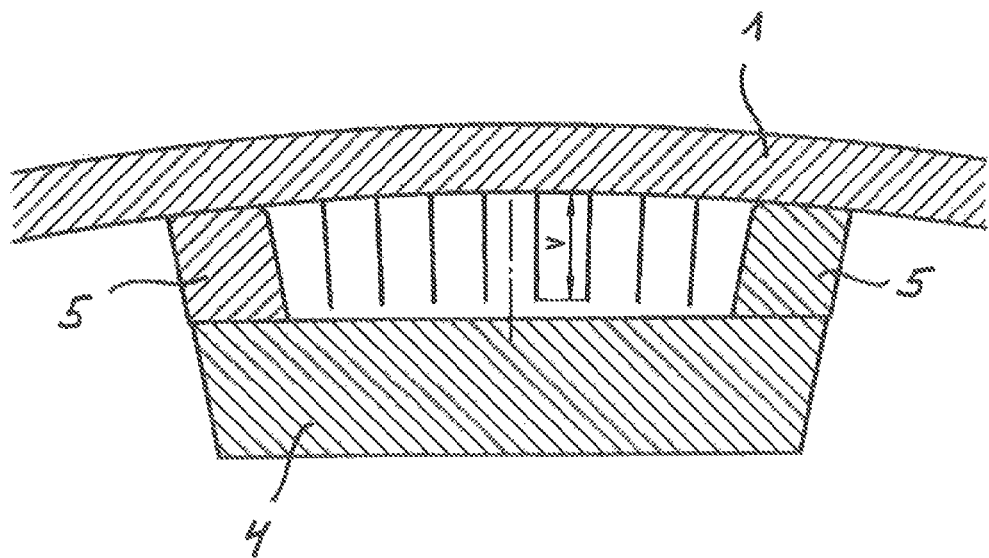
Figure 3:
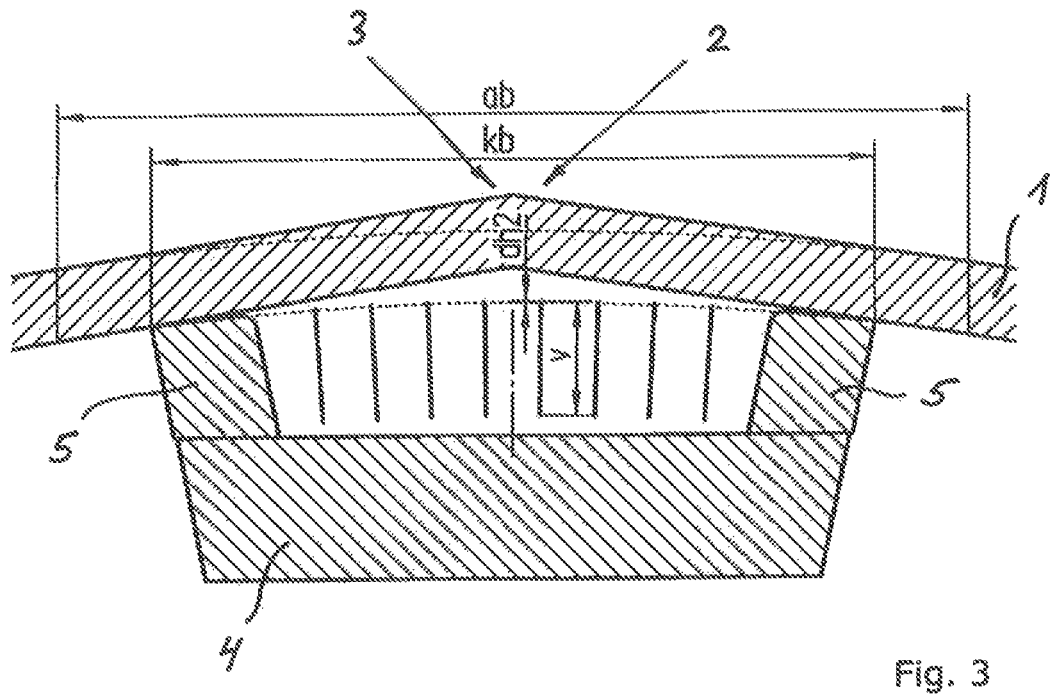
Figure 4:
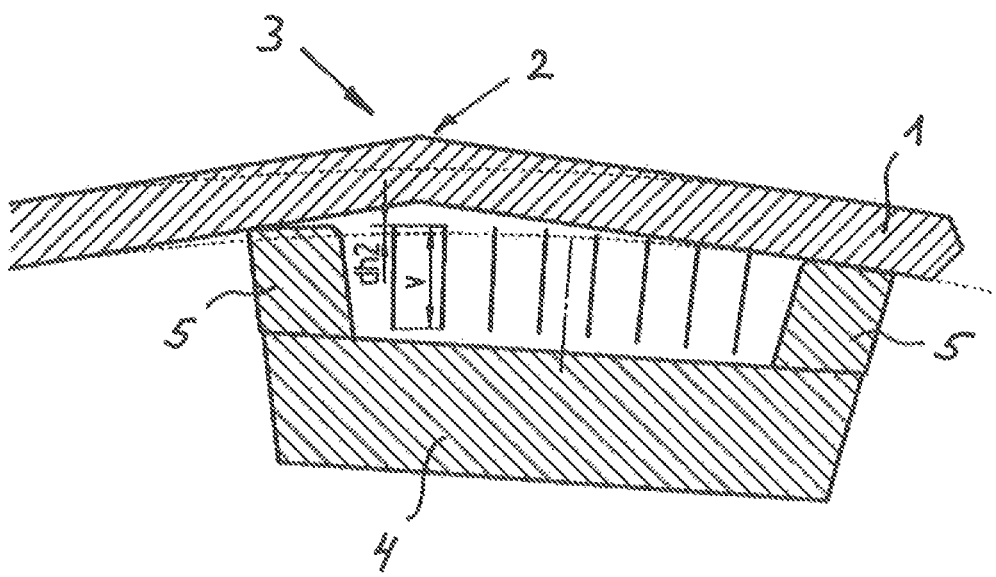
Figure 5:
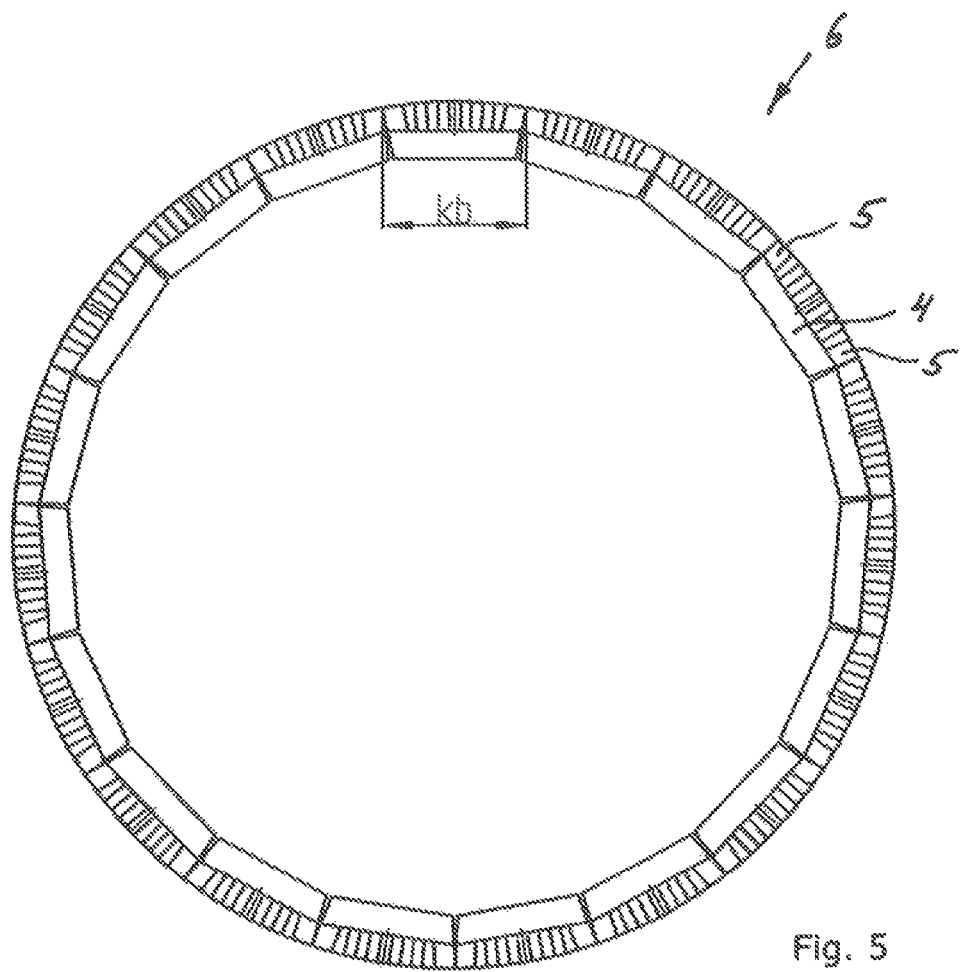
Figure 6:
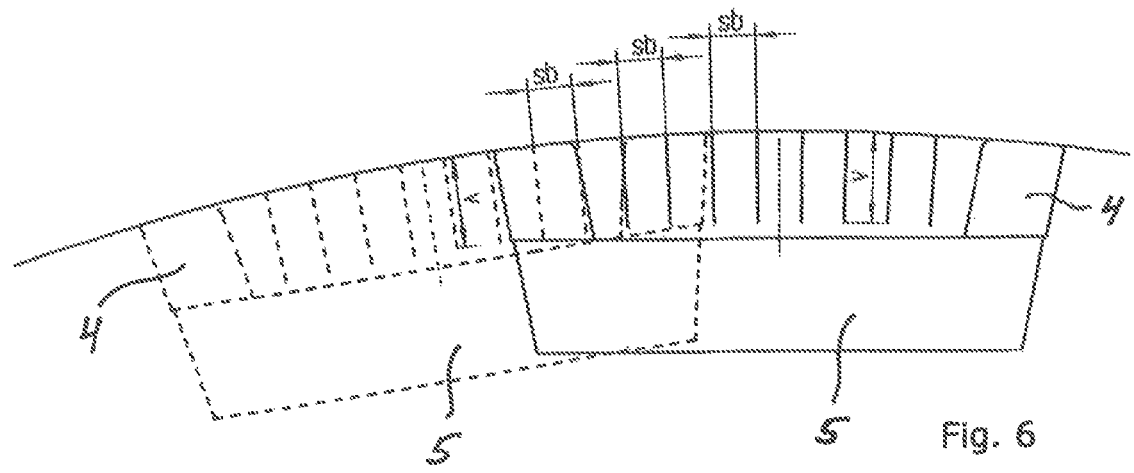
Figure 7:
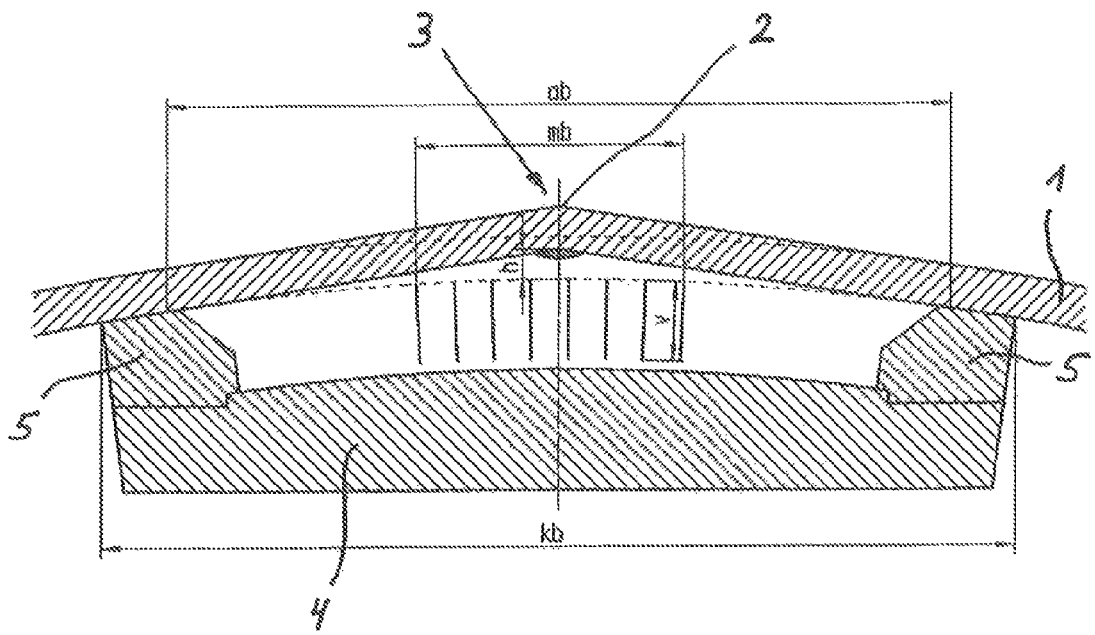
Figure 8:
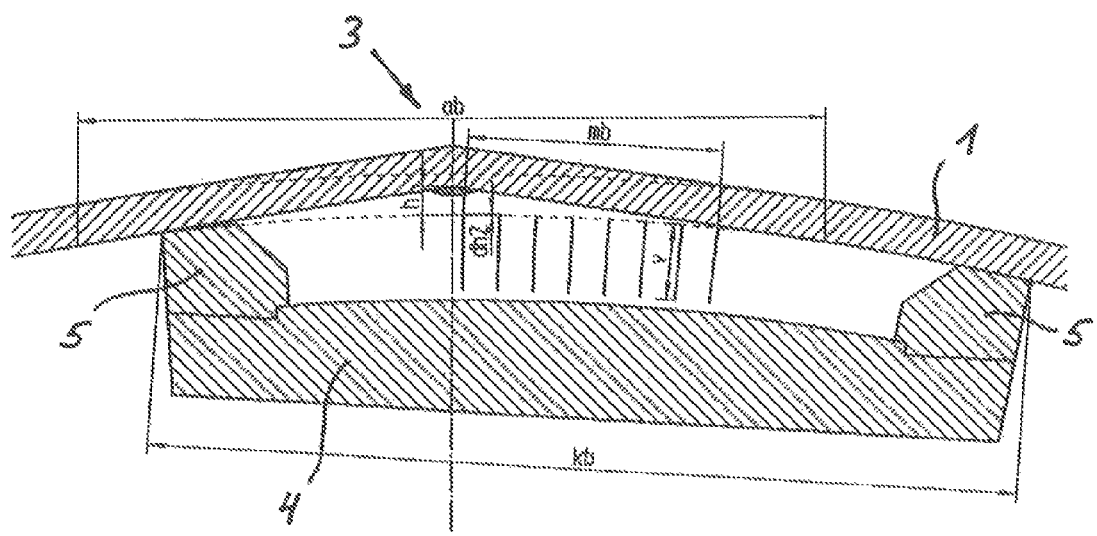
Figure 9:
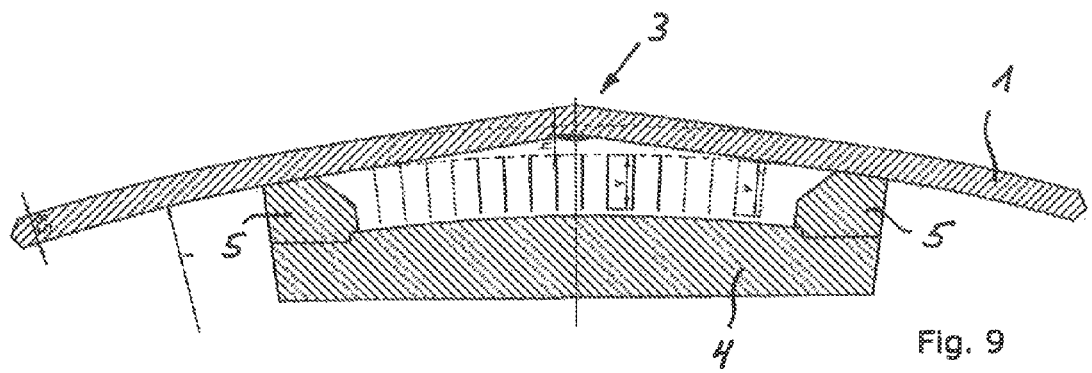
Figure 10:
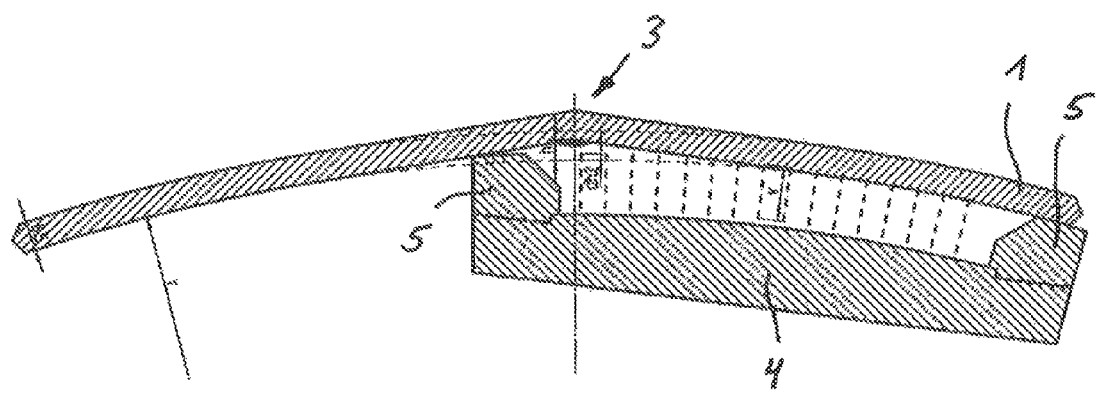
Figure 11:
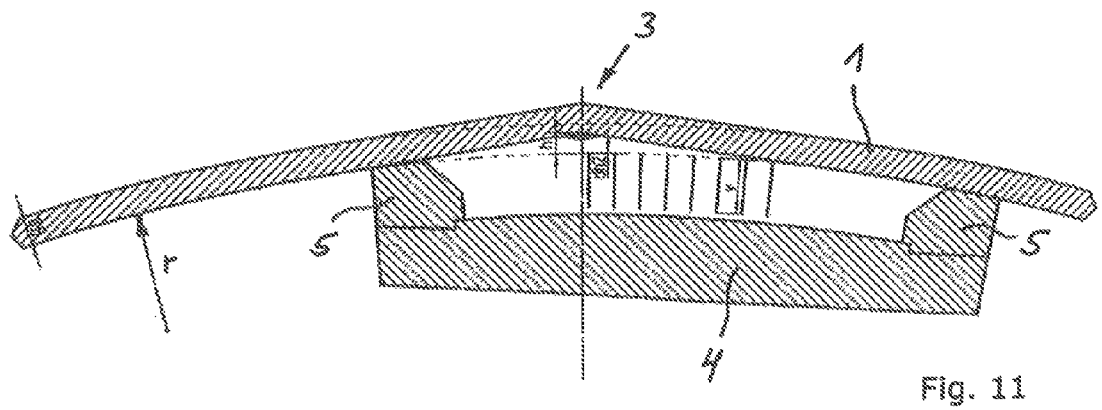
Figure 12:
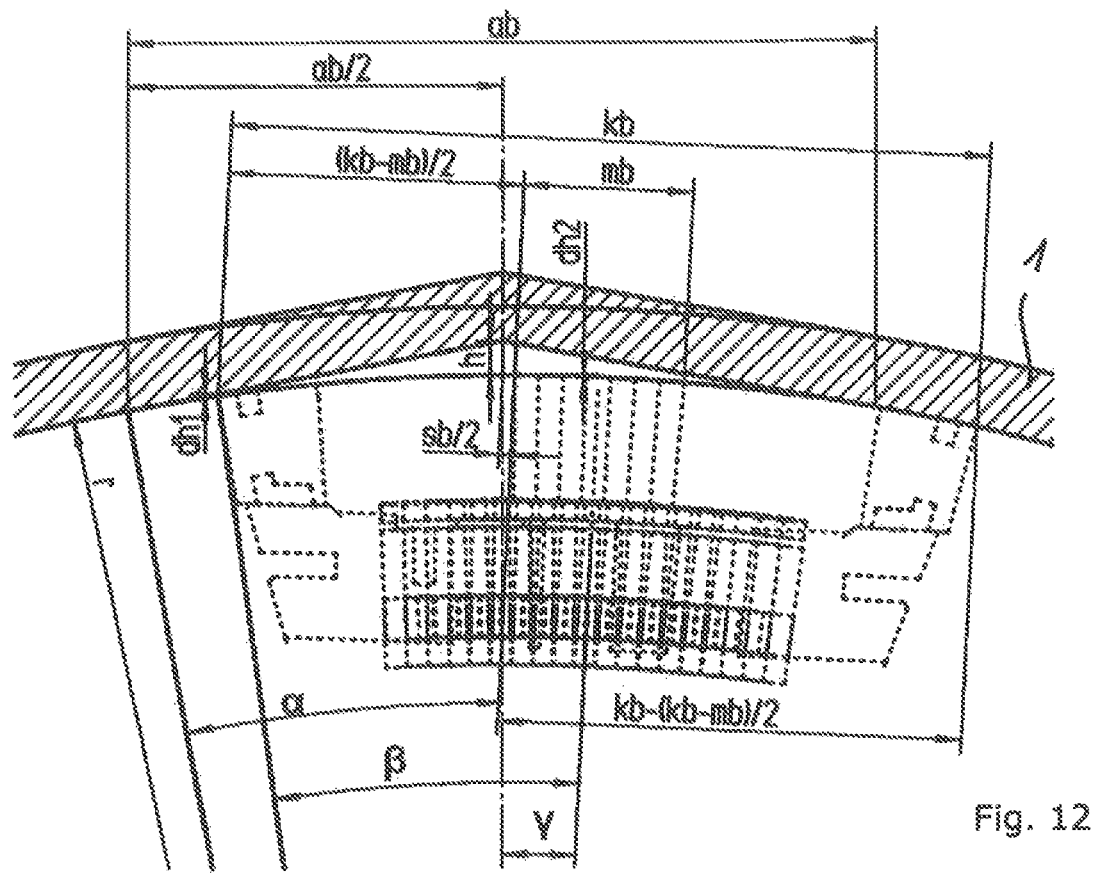
Figure 13:
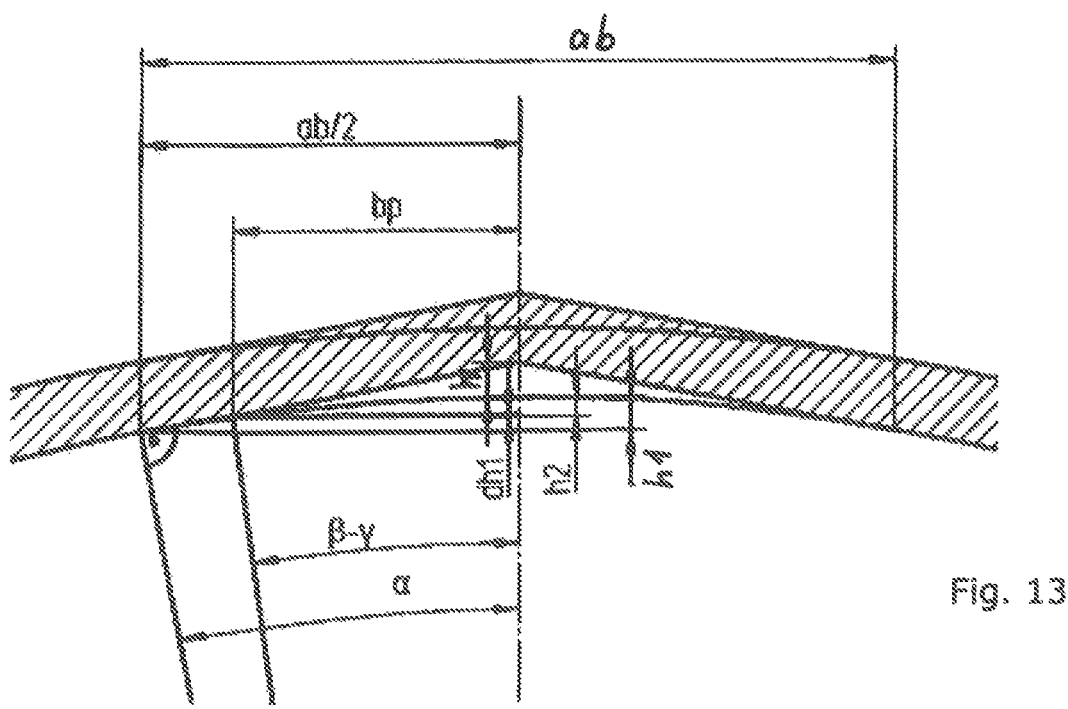
Figure 14:
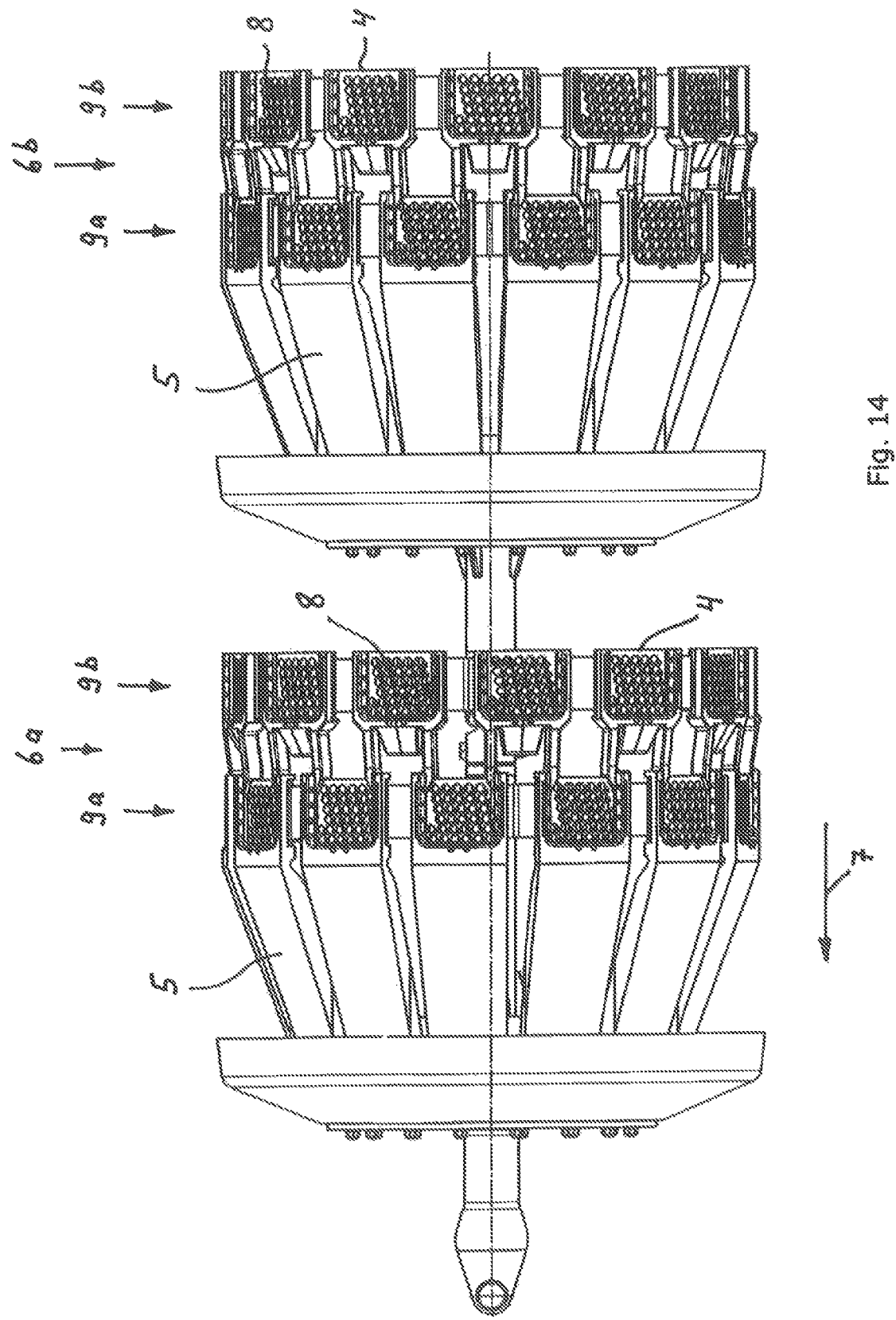
Figure 15:
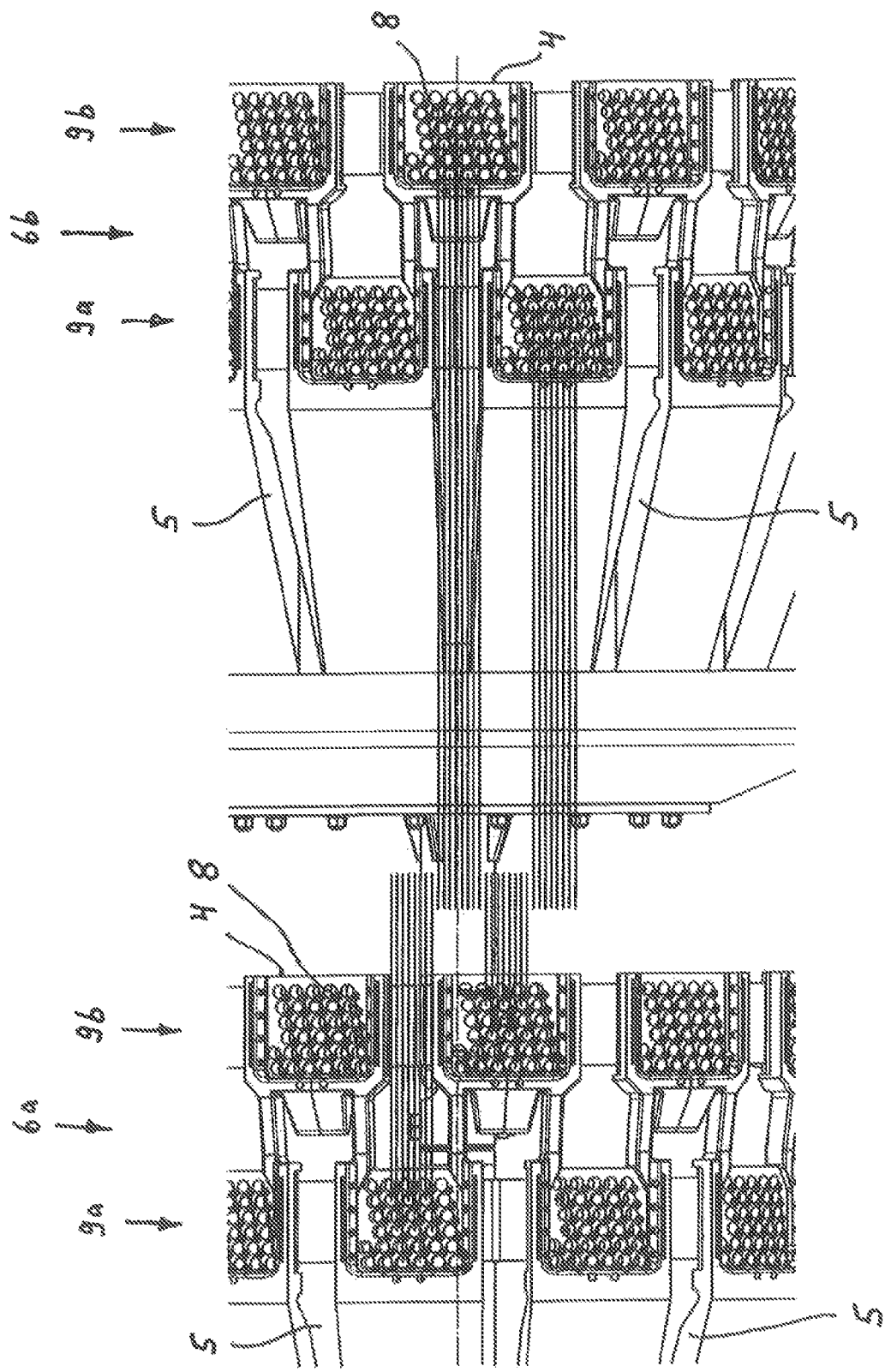
Figure 16:
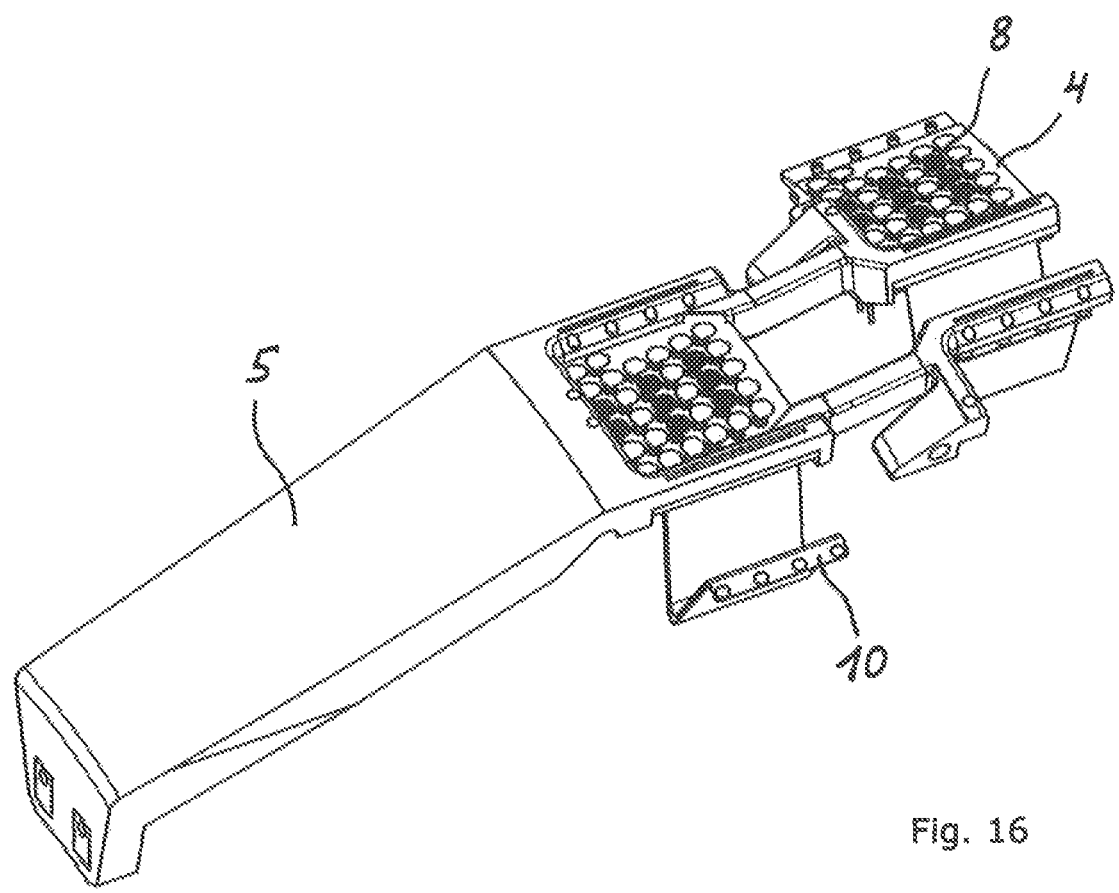

In the drawings:

FIG. 1 is a partial cross-section through a longitudinally welded pipe having a seam peaking, FIG. 2 is a partial cross-section through a longitudinally welded pipe not having seam peaking, during stand off measurement according to the prior art, FIG. 3 is a partial cross-section through a longitudinally welded pipe having seam peaking, during stand off measurement according to the prior art, with the skid in a first position, FIG. 4 is a partial cross-section through a longitudinally welded pipe having seam peaking, during stand off measurement according to the prior art, with the skid in a second position, FIG. 5 is a partial cross-section through a sensor mount according to the prior art, FIG. 6 shows a detail of FIG. 5, FIG. 7 is a partial cross-section through a longitudinally welded pipe having seam peaking, during stand off measurement according to the invention, with the skid in a first position, FIG. 8 is a partial cross-section through a longitudinally welded pipe having seam peaking, during stand oft measurement according to the invention, with the skid in a second position, FIG. 9 is a partial cross-section through a longitudinally welded pipe having seam peaking, during stand off measurement according to the prior art and stand off measurement according to the invention, with the skid in a first position, FIG. 10 is a partial cross-section through a longitudinally welded pipe having seam peaking, during stand off measurement according to the prior art, with the skid in a second position, FIG. 11 is a partial cross-section through a longitudinally welded pipe having seam peaking, during stand off measurement according to the invention, with the skid in a third position, FIG. 12 is a partial cross-section through a longitudinally welded pipe having a seam peaking, during stand off measurement according to the invention, for calculation of the maximum stand off deviation, FIG. 13 shows a detail of FIG. 12, FIG. 14 shows a two-part sensor mount, FIG. 15 shows the sensor track distribution of FIG. 14, and FIG. 16 shows a skid as illustrated in FIG. 14.

FIG. 1 is a partial cross-section through a longitudinally welded pipe 1 of radius r. It deviates from the ideal circular form in that it has a seam peak 3 of height h in the region of the welded seam 2. In a pipe in which r=503.5 mm, the height h of the seam peak can be up to 6 mm. Ultrasonic measurement of cracks at the welded seam 2 with high seam peaking is only possible with geometric limitation, since the intromission angle can vary widely, e.g. with the seam peak 3 shown of 6 mm in a 40-inch diameter pipeline, theoretically up to 8.8°. The so-called central angle of the seam peak 3 is in this example equal to 180°−2·8.8°=162.4°.

FIG. 2 is a partial cross-section through a longitudinally welded pipe 1 analogous to FIG. 1, but without any seam peaking, during stand off measurement according to the prior art. The ultrasonic sensors are mounted on sensor holders 4, which are mounted on movable, flexible, spring-biased skids 5 that are pressed radially outward so as to cause them to bear against the internal surface of the pipe 1. The skids 5 are part of a sensor mount, which is moved through the pipe 1, for example as part of an inline inspection tool. The ultrasonic sensors are disposed throughout the region of a sensor holder 4 between the skids 5. For measurement of the wall thickness of pipe 1, the stand off v from the ultrasonic sensors to the pipe internal wall is also determined, in the example shown, the stand off is, for example, 16 mm.

FIG. 3 is a partial cross-section through a longitudinally welded pipe 1 analogous to FIG. 2, but having a seam peak 3, which is measured according to the prior art, in a first position of the skid 5, when the skid 5 is disposed centrally beneath the welded seam 2, that is to say, exactly centrally beneath the seam peak 3. The skid 5 has a breadth kb, which breadth is the maximum distance across the contact surface by means of which the skid bears against the pipe wall. The seam peak 3 extends across a seam peak breadth ab. By "seam peak breadth" ab is meant the breadth of that region where the actual pipe wall rises away from the ideal pipe wall due to the seam peak 3. Since, in this example, the skid 5 has a width kb of 99 mm and is smaller than the seam peak breadth ab of 125 mm of the seam peak 3, the skid 5 plunges at both sides somewhat into the seam peak 3. The measured stand off v of 16 mm to the pipe wall 1 is thus shortened by 0.22 mm. This gives a stand off deviation dh2 of 0.22 mm.

FIG. 4 is a partial cross-section through a longitudinally welded pipe 1 having a seam peak 3, during stand off measurement according to the prior art in a second position of the skid 5. Compared with FIG. 3, the skid 5 is rotated at an angle to the seam peak 3 and therefore only one side thereof plunges into the seam peak 3. This gives a stand off deviation dh2 of up to 1.26 mm. Due to rotation of the sensor mount carrying the skids 5, the sensor holders 4, and the sensors, about the direction of travel during ultrasonic measurement, it is impossible to predict or to fix the position of the skids 5 relative to a seam peak 3, and thus for geometric reasons a large stand off deviation of 1.26 mm needs to be taken into account when evaluating the measurement results and when removing pipe sections having seam peaks with a threshold size. This large stand off deviation constitutes a systematic error of such seam peaking measurement. As a result, more pipes than necessary have to be replaced when measurement is carried out according to the prior art. In addition, in the case of seam peaking measurement carried out according to the prior art in which the sensors are mounted on rigid, rather than movable, skids 5, the stand off v increases still further. Previous attempts to prevent or minimize plunging of the skids 5 into the seam peak 3 by using a rigid sensor mount have hitherto produced varying stand offs, since the rigid sensor mount could not, on account of its weight, assume a central position. With such a procedure, it is not possible to measure the wall thickness at the same time.

FIG. 5 is a cross-section through a sensor mount 6 according to the prior art, and FIG. 6 shows a detail of FIG. 5. The sensor mount 6 includes skids 5 having a breadth kb of 99 mm. A skid 5 is designed with sufficient width that half of the skids when laid beside one another cover a circumference of 85% of the external diameter of the pipe (note that the sensor mount 6 has two rings disposed one behind the other), that is to say, the sensor mount has a size reducibility of 85%, and at the same time the skid 5 can accommodate enough sensors to ensure that full coverage can be achieved even at the largest diameter, that is to say, over the entire circumference all sensors are spaced apart by the same distance X.

FIG. 7 is a partial cross-section through a longitudinally welded pipe 1 having a seam peak 3, during stand off measurement according to the invention, in a first position of the skid 5, which position corresponds to that shown in FIG. 3. FIG. 8 shows a partial cross-section through the longitudinally welded pipe 1 having a seam peak 3, during stand off measurement according to the invention in a second position of the skid 5, which corresponds roughly to the position shown in FIG. 4.

A method according to the invention for measuring seam peaking in a pipe 1, more particularly in a pipeline, by means of ultrasonic measurement with the aid of ultrasonic probes mounted on sensor holders 4 attached to a sensor mount, which is moved in a direction of transport through the pipe 1, is characterized in that a sensor mount is used that has sensor holders 4 that are mounted on movable skids 5, which skids 5 are pressed radially outward by means of spring elements to cause them to bear against the internal surface of the pipe 1 such that the sensor mount has a size reducibility and such that the sensors are at a fixed stand off v from the internal surface of the pipe 1 when outside a region of a seam peak 3. Therein skids 5 are used that have a large skid breadth kb, which is larger than the seam peak breadth ab measured in the circumferential direction of the pipe 1 in the region of a seam peak 3 to be measured. Furthermore, the sensor holders 4 are equipped in each case with sensors located only in a measuring region that is situated half way between two skid contact surfaces, wherein the breadth of the measuring region mb is either smaller than, or equal to, half of the skid breadth kb, so that the stand off deviation dh2 of the sensors resulting in the region of a seam peak 3 remains below a given threshold value. Furthermore, a sensor mount is used that has at least three successive rings disposed one behind the other as regarded in the direction of transport of the sensor mount, and has sensors carried by sensor holders 4, wherein the sensors are disposed on the respective rings with a track distance and the sensors on the succeeding rings are in a gap-covering manner in staggered relationship to each other, thus achieving full coverage of the tracks over the circumference of the pipe 1.

Minimization of the stand off deviation dh2 is achieved due to the fact that the breadth kb of the skid 5 is greater than the seam peak breadth of the seam peak 3 to be measured, and is thus also greater than the breadth of the measuring area of the sensors, i.e. the breadth mb of the measuring region. At the same time, the breadth nib of the sensor measuring region is sufficiently small that the maximum stand off deviation dh2 remains small to minimal when the position of the skid 5 relative to the seam peak 3 changes. The measuring region, i.e. the measuring area of the sensors, is in the center of the skid 5, but not at the edge where the skid 5 bears against the pipe wall. In the example shown the pipe diameter is, say, from 34 inches to 40 inches. The seam peak height is from 5 mm to 6 mm. When the skid breadth kb is less than half of the seam peak breadth and the other conditions described hold, the stand off deviation dh2 in this example is less than 0.18 mm.

FIGS. 9 to 11 illustrate the change in stand off dh2 in the seam peak 3 as a function of the position of the skid 5 relative to the seam peak 3 for the example shown in FIGS. 7 and 8 and for a pipe 1 with r=503.5 mm, a wall thickness of 8.5 mm and a seam peak height h of 6 mm. Furthermore, FIG. 9 is a partial cross-section through a longitudinally welded pipe 1 having a seam peak 3, during stand off measurement according to the prior art (dashed lines=stand offs v) and stand off measurement according to the invention (solid lines=stand offs v) in a first, midway position of the skid 5. FIG. 10 is a partial cross-section through a longitudinally welded pipe 1 having a seam peak 3, during stand off measurement according to the prior art, in a second, rotated position of the skid 5. Herein the maximum stand off deviation dh2 with a full complement of sensors according to the prior art on the sensor holders 4 is 1.88 mm. FIG. 11 is a partial cross-section through a longitudinally welded pipe 1 having a seam peak 3 during stand off measurement according to the invention, in a third, rotated position of skid 5, while in this position the stand off deviation dh2 according to the invention is only 0.18 mm. Thus, stand off measurement according to the invention provides a much more exact statement concerning the measured stand off and consequently concerning the height of the seam peak, even when the skid 5 is guided in a flexible manner along the pipe's internal wall.

The invention provides the technical prerequisites to enable an exact stand off measurement to be carried out using flexible skids. The multipart sensor mount allows the skids to be widened while still maintaining its ease of passage through the pipeline. The distribution of the sensors on and around the sensor holder is such as to ensure optimal coverage of the pipe circumference and, simultaneously, to ensure that the theoretical stand off deviation is minimal. This makes it possible for the size of the stand off used for seam peaking measurement to be in the range appropriate for measurement of wall thickness, enabling the two measurements to be carried out simultaneously.

FIG. 12 is a partial cross-section through a longitudinally welded pipe 1 having seam peaking during stand off measurement according to the invention for calculation of the maximum stand off deviation dh2. FIG. 13 shows a detail of FIG. 12. These figures demonstrate the effect of skid geometry on the accuracy of measurement. The maximum theoretical stand off deviation dh2 depends on the skid breadth kb, the breadth mb of the measuring region, the pipe radius r and the sensor track distance sb. The sensor track distance sb is the distance between the imaginary echo points on the pipe wall from one sensor to the next and is a measure of the accuracy of the measurement. For a maximum theoretical stand off deviation dh2 of 0.25 mm with a seam peak height h of up to 5 mm, the value of (kb−mb−sb)/ab must be greater than 0.72. It is suggested as a preferred feature for an appropriate method for measuring seam peaks 3 that are smaller than 5 mm, and for a maximum stand off deviation dh2 that is smaller than 0.25 mm, for the skid breadth kb, the measuring region breadth mb, and the sensor track distance sb to be such that for a pipe radius r and a seam peak breadth ab the following should hold: (kb−mb−sb)/ab>0.72.

This relationship is explained by use of the following calculation examples with reference to FIGS. 12 and 13. These values are determined for a maximum seam peak height h of 5 mm. The threshold value varies with the assumed maximum seam peak 3. In the figures, $\alpha$ is the angle of the seam peak 3, $\beta$ is the angle across half of the skid breadth kb, and $\gamma$ is the angle of the maximum deflection of the skid 5. The other values can be taken from the figures or from the following calculations.

EXAMPLE 1

Construction with a Stand Off Deviation dh2<0.25 mm

Given:

| | |
|---|---|
| Skid breadth | kb = 108.85 mm |
| Measurement region breadth | mb = 24.45 mm |
| Pipe radius | r = 294.8 mm |
| Seam peak height | h = 5 mm |

Calculation of the Stand Off Deviation dh2:

$$\alpha = a\cos\left(\frac{r}{r+h}\right) = 0.183$$

$$\beta = a\sin\left(\frac{kb}{2r}\right) = 0.186$$

$$\gamma = a\sin\left(mb \cdot \frac{8}{14 \cdot r}\right) = 0.047$$

$$ab = \sin(\alpha) \cdot r \cdot 2 = 107.232 \text{ mm}$$

$$h1 = \left(\tan(\alpha) \cdot \frac{ab}{2}\right) - h = 4.917 \text{ mm}$$

$$h2 = r - (\cos(\beta - \gamma) \cdot r) = 2.814 \text{ mm}$$

$$bp = \sin(\beta - \gamma) \cdot r = 40.633 \text{ mm}$$

$$dh1 = -\left[\frac{2 \cdot (h1 + h2) \cdot bp}{ab}\right] + h + h2 = 0.298 \text{ mm}$$

$$dh2 = \frac{dh1}{kb} \cdot \left[kb - \frac{(kb - mb)}{2}\right] = 0.183 \text{ mm}$$

$$dh2 = \frac{-\tan(\alpha) \cdot \sin(\beta - \gamma) \cdot r + h + [r - \cos(\beta - \gamma) \cdot r]}{kb} \cdot \frac{kb + mb}{2}$$

Calculation of the Threshold Value gw:

$$sb = \frac{mb}{7} = 3.493 \text{ mm}$$

$$gw = \frac{(kb - mb - sb)}{ab} = 0.755$$

EXAMPLE 2

Given:

| | |
|---|---|
| Skid breadth | kb = 104.54 mm |
| Measurement region breadth | mb = 24.45 mm |
| Pipe radius | r = 294.8 mm |
| Seam peak height | h = 5 mm |

Calculation of the Stand Off Deviation dh2:

$$\alpha = a\cos\left(\frac{r}{r+h}\right) = 0.183$$

$$\beta = a\sin\left(\frac{kb}{2r}\right) = 0.178$$

$$\gamma = a\sin\left(mb \cdot \frac{8}{14 \cdot r}\right) = 0.047$$

$$ab = \sin(\alpha) \cdot r \cdot 2 = 107.232 \text{ mm}$$

$$h1 = \left(\tan(\alpha) \cdot \frac{ab}{2}\right) - h = 4.917 \text{ mm}$$

$$h2 = r - (\cos(\beta - \gamma) \cdot r) = 2.52 \text{ mm}$$

$$bp = \sin(\beta - \gamma) \cdot r = 38.461 \text{ mm}$$

$$dh1 = -\left[\frac{2 \cdot (h1 + h2) \cdot bp}{ab}\right] + h + h2 = 0.406 \text{ mm}$$

$$dh2 = \frac{dh1}{kb} \cdot \left[kb - \frac{(kb - mb)}{2}\right] = 0.251 \text{ mm}$$

Calculation of the Threshold Value gw:

$$sb = \frac{mb}{7} = 3.493 \text{ mm}$$

$$gw = \frac{(kb - mb - sb)}{ab} = 0.714$$

The skid is too narrow, and thus the stand off deviation dh2 is greater than 0.25 mm and the threshold value gw is less than 0.72.

EXAMPLE 3

Given:

| | |
|---|---|
| Skid breadth | kb = 108.85 mm |
| Measurement region breadth | mb = 28.10 mm |
| Pipe radius | r = 294.8 mm |
| Seam peak height | h = 5 mm |

Calculation of the Stand Off Deviation dh2:

$$\alpha = a\cos\left(\frac{r}{r+h}\right) = 0.183$$

$$\beta = a\sin\left(\frac{kb}{2r}\right) = 0.186$$

$$\gamma = a\sin\left(mb \cdot \frac{8}{14 \cdot r}\right) = 0.054$$

$$ab = \sin(\alpha) \cdot r \cdot 2 = 107.232 \text{ mm}$$

$$h1 = \left(\tan(\alpha) \cdot \frac{ab}{2}\right) - h = 4.917 \text{ mm}$$

$$h2 = r - (\cos(\beta - \gamma) \cdot r) = 2.533 \text{ mm}$$

$$bp = \sin(\beta - \gamma) \cdot r = 38.536 \text{ mm}$$

$$dh1 = -\left[\frac{2 \cdot (h1 + h2) \cdot bp}{ab}\right] + h + h2 = 0.401 \text{ mm}$$

$$dh2 = \frac{dh1}{kb} \cdot \left[kb - \frac{(kb - mb)}{2}\right] = 0.252 \text{ mm}$$

Calculation of the Threshold Value gw:

$$sb = \frac{mb}{7} = 4.014 \text{ mm}$$

$$gw = \frac{(kb - mb - sb)}{ab} = 0.716$$

The measuring region rib is too broad, and thus the stand off deviation dh2 is greater than 0.25 mm and the threshold value gw is less than 0.72.

FIG. 14 shows a two-part sensor mount 6 for carrying out stand off measurement in a pipeline according to the invention. The sensor mount 6 can be part of an inline inspection tool and is moved in a direction of transport 7 through the pipe (not shown). The sensor mount 6 includes a front sensor mount 6a and a rear sensor mount 6b having sensors 8 mounted on sensor holders 4, which are moved along the internal surface of the pipe on movable, flexible skids 5. These skids 5 are pressed radially outward by means of spring elements, in order to make them bear against the internal surface of the pipe. Each part 6a, 6b of the sensor mount 6 includes two rings 9a, 9b, disposed one behind the other, these having sensors 8 disposed in staggered relationship to one another so as to cover gaps on the other ring, thus achieving full coverage of the circumference of the pipe. Since the skids 5 are broader than in the prior art, the number of skids 5 per ring 9 needs to be halved in order to achieve a size reducibility of 85%. In order to achieve full coverage using fewer sensors 8 per skid 5, a second sensor mount 6b is disposed behind the first sensor mount 6a, in staggered relationship thereto so as to cover the gaps of that first sensor mount. FIG. 15 shows the distribution of sensor tracks illustrated in FIG. 14 and the distribution of the sensors 8 (sensor tracks) on the sensor mounts 6a, 6b. The sensor tracks are preferably distributed uniformly over the circumference of the pipe. With such an arrangement, it is possible to carry out seam peaking measurement and wall thickness measurement at the same time.

FIG. 16 shows a skid 5 illustrated in FIG. 15 and having sensor holders 4 with a complement of sensors 8. The skids 5 are interconnected by spring elements 10 to ensure that the skids 5 always bear against the internal surface of the pipe and the sensors 8 are at a constant stand off v (constant in terms of minimum stand off deviation dh2), such as is usual for any conventional wall thickness measurement.

LIST OF REFERENCE NUMERALS OR CHARACTERS 1 pipe
2 welded seam
3 seam peak
4 sensor holder
5 skid
6 sensor mount
7 direction of transport
8 sensor
9 ring
10 spring element
ab seam peak breadth
dh2 stand off deviation
gw threshold value
h height of the seam peak
kb skid breadth
mb breadth of the measuring region
r pipe radius
sb track distance of the sensors
v stand off
X distance
α angle of peak
β angle of skid breadth/2
γ angle of maximum deflection of skid

The invention claimed is:

1. A method for measuring seam peaking in a pipe, more particularly in a pipeline, by means of ultrasonic measurement with the aid of ultrasonic probes mounted on sensor holders attached to a sensor mount, which is moved in a direction of transport through said pipe, wherein the sensor mount used is a sensor mount on which the sensor holders are mounted on movable skids, which movable skids are pressed radially outward by means of spring elements so as to cause the movable skids to bear against an internal surface of said pipe, such that said sensor mount has a size reducibility and such that sensors used as said ultrasonic probes are at a fixed stand off from said internal surface of said pipe except for a region of a seam peak, the movable skids used are movable skids that have a large skid breadth, which is greater than a seam peak breadth measured in a circumferential direction of the pipe in the region of the seam peak to be measured, and said sensor holders are equipped in each case with the sensors only in a measuring region that is situated half way between two skid contact surfaces, wherein the breadth of the measuring region is smaller than, or equal to, half of the skid breadth, such that a stand off deviation of the sensors resulting in the region of the seam peak remains below a specified threshold value, and said sensor mount comprises at least three successive rings, wherein the rings are disposed one behind the other as regarded in the direction of transport of said sensor mount and have the sensors carried by the sensor holders, wherein said sensors are disposed on the respective rings with a track distance and the sensors on the succeeding rings are in a gap-covering manner in staggered relationship to each other, thus achieving full coverage of tracks of the sensors over a circumference of said pipe.

2. The method of claim 1, wherein the seam peak is measured in the pipe and the diameter of the pipe is between 25 cm and 135 cm.

3. The method of claim 1, wherein a maximum stand off deviation is less than 0.25 mm.

4. The method of claim 1, wherein a maximum stand off deviation is less than 0.18 mm.

5. The method of claim 1, wherein the seam peak measured is a seam peak that is less than 6 mm.

6. The method of claim 1, wherein the seam peak measured is a seam peak that is less than 5 mm.

7. The method of claim 1, wherein the breadth of the measuring region is between 5% and 50% of the skid breadth.

8. The method of claim 1, wherein the breadth of the measuring region is between 10% and 45% of the skid breadth.

9. The method of claim 1, wherein the breadth of the measuring region is between 20% and 35% of the skid breadth.

10. The method of claim 1, wherein for the measurement of the seam peak which is a seam peak that is smaller than 5 mm, and for a maximum stand off deviation that is smaller than 0.25 mm, the skid breadth, the breadth of the measuring region and the track distance of said sensors are selected such that for a pipe radius and the seam peak breadth the following applies: (kb-mb-sb/ab)>0.72.

11. The method of claim 1, wherein a stand off is used that enables a simultaneous wall thickness measurement of the pipe to be carried out, and the wall thickness measurement is concurrently carried out with said seam peaking measurement.

12. The method of claim 1, wherein the track distance is uniformly distributed over the circumference.

13. A sensor mount for the execution of the method according to claim 1 for measuring seam peaking in a pipe, which sensor mount is capable of moving in a direction of transport through said pipe and comprises sensor holders, on which ultrasonic probes are mounted for the purpose of carrying out an ultrasonic measurement, wherein said sensor mount comprises movable skids, on which said sensor holders are mounted, and comprises spring elements, by means of which said skids are pressed radially outward such that said skids are caused to bear against internal surface of said pipe such that said sensor mount has a size reducibility and such that sensors used as said ultrasonic probes are at a fixed stand off from said internal surface of said pipe except for a region of a seam peak, wherein said skids have a large skid breadth that is greater than a seam peak breadth measured in a circumferential direction of said pipe in the region of the seam peak to be measured, and said sensor holders are equipped in each case with the sensors only in a measuring region that is situated half way between two skid contact surfaces, wherein the breadth of the measuring region is smaller than, or equal to, half of the skid breadth, such that a stand off deviation of the sensors resulting in the region of the seam peak remains below a specified threshold value, and said sensor mount comprises at least three successive rings, wherein the rings are disposed one behind the other as regarded in the direction of transport of said sensor mount and have sensors carried by the sensor holders, wherein said sensors are disposed on the respective rings with a track distance and the sensors on the succeeding rings are in a gap-covering manner in staggered relationship to each other, thus achieving full coverage of tracks of the sensors over a circumference of said pipe.

14. The sensor mount of claim 13, wherein the sensor mount is adapted for measuring the seam peak in the pipe and the diameter of the pipe is between 25 cm and 135 cm.

15. The sensor mount of claim 13, wherein the sensor mount is adapted such that a maximum stand off deviation is less than 0.25 mm.

16. The sensor mount of claim 13, wherein the sensor mount is adapted such that a maximum stand off deviation is less than 0.18 mm.

17. The sensor mount of claim 13, wherein the sensor mount is adapted for measuring the seam peak that and the seam peak is less than 6 mm.

18. The sensor mount of claim 13, wherein the sensor mount is adapted for measuring the seam peak and the seam peak is less than 5 mm.

19. The sensor mount of claim 13, wherein the breadth of said measuring region is between 5% and 50% of the skid breadth.

20. The sensor mount of claim 13, wherein the breadth of said measuring region is between 10% and 45% of the skid breadth.

21. The sensor mount of claim 13, wherein the breadth of said measuring region is between 20% and 35% of the skid breadth.

22. The sensor mount of claim 13, wherein the track distance is uniformly distributed over the circumference.

23. An inline inspection tool for carrying out a measurement of seam peaking in a pipe, more particularly in a pipeline, which comprises at least one sensor mount according to claim 13.

* * * * *